(12) United States Patent
Nath

(10) Patent No.: US 6,749,616 B1
(45) Date of Patent: Jun. 15, 2004

(54) SURGICAL SYSTEM FOR REPAIRING AND GRAFTING SEVERED NERVES AND METHODS OF REPAIRING AND GRAFTING SEVERED NERVES

(75) Inventor: Rahul Nath, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 189 days.

(21) Appl. No.: 09/989,963

(22) Filed: Nov. 21, 2001

(51) Int. Cl.$^7$ ................................................ A61B 17/04
(52) U.S. Cl. ...................................... 606/152; 606/224
(58) Field of Search ................................. 606/152, 224

(56) References Cited

U.S. PATENT DOCUMENTS

| | | | |
|---|---|---|---|
| 3,716,058 A | 2/1973 | Tanner, Jr. | |
| 3,960,151 A | 6/1976 | Kuhn | |
| 4,573,576 A | 3/1986 | Krol | |
| 4,778,467 A | 10/1988 | Stensaas et al. | |
| 4,883,618 A | 11/1989 | Barrows | |
| 5,147,399 A | 9/1992 | Dellon et al. | |
| 5,160,339 A | * 11/1992 | Chen et al. | 606/158 |
| 5,318,543 A | 6/1994 | Ross et al. | |
| 5,330,442 A | * 7/1994 | Green et al. | 606/232 |
| 5,354,305 A | 10/1994 | Lewis, Jr. et al. | |
| 5,376,101 A | * 12/1994 | Green et al. | 606/232 |
| 5,391,182 A | 2/1995 | Chin | |
| 5,392,917 A | * 2/1995 | Alpern et al. | 206/570 |
| 5,437,680 A | * 8/1995 | Yoon | 606/139 |
| 5,520,702 A | * 5/1996 | Sauer et al. | 606/144 |
| 5,562,683 A | 10/1996 | Chan | |
| 5,669,917 A | * 9/1997 | Sauer et al. | 606/139 |
| 5,683,417 A | * 11/1997 | Cooper | 606/223 |
| 5,690,655 A | 11/1997 | Hart et al. | |
| 5,746,752 A | 5/1998 | Burkhart | |
| 5,766,234 A | * 6/1998 | Chen et al. | 607/92 |
| 5,800,447 A | 9/1998 | Wenstrom, Jr. | |
| 5,951,590 A | * 9/1999 | Goldfarb | 606/232 |
| 5,976,159 A | * 11/1999 | Bolduc et al. | 606/142 |
| 5,984,933 A | * 11/1999 | Yoon | 606/148 |
| 6,001,109 A | 12/1999 | Kontos | |
| 6,102,921 A | 8/2000 | Zhu et al. | |
| 6,607,541 B1 | * 8/2003 | Gardiner et al. | 606/151 |
| 2002/0069884 A1 | * 6/2002 | Boyd et al. | 128/898 |

* cited by examiner

*Primary Examiner*—Gary Jackson
(74) *Attorney, Agent, or Firm*—Anthony F. Matheny; Andrews Kurth LLP

(57) ABSTRACT

The invention relates to a surgical system for repairing severed nerve ends. The severed nerve ends may be located on a single nerve or may be located on a nerve graft and a severed nerve. The surgical system includes a suture having a needle and an expanded tail, a clip, and a retaining member. Methods of repairing severed nerve ends and methods of adjoining severed nerve ends are also disclosed.

19 Claims, 2 Drawing Sheets

SURGICAL SYSTEM FOR REPAIRING AND GRAFTING SEVERED NERVES AND METHODS OF REPAIRING AND GRAFTING SEVERED NERVES

BACKGROUND OF THE INVENTION

1. Field of the Invention

This invention relates to a surgical system and method for the repair of severed peripheral nerves, and in particular, to a surgical system for cavernous nerve grafting and method of cavernous nerve grafting.

2. Description of Related Art

Injury to a nerve can result in a partial or total loss of the sensation, control, or use of a member or portion of the body. Neurorrhaphy is a surgical procedure for the repair of lacerated or severed peripheral nerves by suturing the ends of a severed nerve together. The use of neurorrhaphy has enhanced the surgeon's ability to reattach amputated body parts, to achieve composite tissue transfer, and to graft nerves. Although neurorrhaphy methods currently exist, such methods are not always possible and are commonly not completely successful in achieving a restoration of sensation, control, and use of the affected portion of the body.

A repair is satisfactory when it is executed with as little trauma as possible and when alignment of the severed nerve ends is achieved. It is difficult to fulfill the requirements without magnification, micro-surgical instruments, and the finest of sutures. Despite the advances that have been made to date, the re-establishment of normal function in the damaged nerve is difficult to achieve.

The success of such procedures is still limited because the current methods of suturing severed nerves is difficult, time-consuming, and often yields poor functional results due to a variety of factors. The most critical factor of technique in neurorrhaphy is the accurate approximation of the cut ends of the fasciculi (nerve bundles within the nerve trunk). Even though other factors may be ideal, the neurorrhaphy will fail if a significant number of fasciculi are not sufficiently aligned. This is because motor axons regenerating through the sheaths of sensory nerves, and vice versa, will give no return of sensory or motor function.

Alignment of the fasciculi may be achieved by visually orienting the fasciculi of the severed ends of the nerve. Alternatively, the fasciculi may be aligned by visually orienting the blood vessels disposed along the length of the severed ends of the nerve. In either approach, an unobstructed view of the severed nerve ends is necessary.

Another factor is the tendency of severed nerve ends to contract and pull apart after suffering damage. Consequently, when connection of the severed nerve ends is attempted, atensile force may be created in the severed ends as they are drawn together, complicating both the process of rejoining the severed ends, and the healing process. For example, during the healing process it is difficult to alleviate the tensile force located at the severed nerve ends. This tensile force may cause the nerve ends to pull loose from the connection, thereby resulting in decreased functional connection of the nerve or nerve graft.

Other techniques involve using a sheath, or cylindrically shaped tube, to encase the nerve in an attempt to maintain the severed nerve ends in proper alignment to facilitate healing, and thus, functional connection of the severed nerve ends. These techniques limit the surgeon's vision thereby hampering the surgeon's ability to align the severed nerve ends. The absence of a cylindrically shaped tube or sheath disposed over the severed nerve, as in the present invention, permits continuous visibility of the anastomotic site during alignment of the severed nerve ends.

Accordingly, prior to the development of the present invention, there has been no surgical system for repairing severed nerves, method of repairing severed nerves, or method of adjoining severed nerves, which: increases the visibility of the anastomotic site thereby facilitating proper alignment of the severed nerve ends; and decreases trauma to the severed nerve ends thereby facilitating healing of the severed nerve. Therefore, the art has sought a surgical system for repairing severed nerves, method of repairing severed nerves, and method of adjoining severed nerves, which: increases the visibility of the anastomotic site thereby facilitating proper alignment of the severed nerve ends; and decreases trauma to the severed nerve ends thereby facilitating healing of the severed nerve. It is believed that the present invention will achieve these objectives and overcome the disadvantages of other surgical systems, methods of repairing severed nerves, and methods of adjoining severed nerves in the field of the invention, but its results or effects are still dependent upon the skill and training of the operators and surgeons.

SUMMARY OF INVENTION

In accordance with the invention the foregoing advantages have been achieved through the present surgical system for repairing severed nerves comprising: at least one suture having a first end and a second end; at least one clip having a support member and at least one arm having a length; and at least one retaining member having a first end and a second end.

A further feature of the surgical system for repairing severed nerves is that the first end of the suture may include a needle. Another feature of the surgical system for repairing severed nerves is that the second end of the suture may include an expanded tail. An additional feature of the surgical system for repairing severed nerves is that the clip may include two arms. Still another feature of the surgical system for repairing severed nerves is that the clip may be formed out of metal. A further feature of the surgical system for repairing severed nerves is that the clip may be formed out of plastic. Another feature of the surgical system for repairing severed nerves is that the clip may be formed out of an absorbable polymer or copolymer. An additional feature of the surgical system for repairing severed nerves is that the retaining member may be formed out of plastic. Still another feature of the surgical system for repairing severed nerves is that the retaining member may be formed out of an absorbable polymer or copolymer. A further feature of the surgical system for repairing severed nerves is that each of the two arms may include equal lengths. Another feature of the surgical system for repairing severed nerves is that each of the two arms may include a length of about 2.5 millimeters. An additional feature of the surgical system for repairing severed nerves is that the support member may include a length of about 1.5 millimeters. Still another feature of the surgical system for repairing severed nerve ends is that the retaining member may include a length of about 3.0 millimeters. A further feature of the surgical system for repairing severed nerves is that the suture may include a length of about 3.0 centimeters.

In accordance with the invention the foregoing advantages have also been achieved through the present method of repairing severed nerves comprising the steps of: providing a severed nerve having a first severed end and a second severed end; forming a suture having a first end and a second end, wherein the first end includes a needle and the second end includes an expanded tail; aligning the first severed end with the second severed end; inserting the needle through the first and second severed ends; securing the expanded tail of the suture to either the first severed end or the second severed end; removing the needle from the first end of the suture; placing the first end of the suture and a retaining member within a clip; and capturing the first end of the suture and the retaining member within the clip.

A further feature of the method of repairing severed nerves is that the first end of the suture and the retaining member may be captured within the clip by deforming the clip. Another feature of the method of repairing severed nerves is that the first end of the suture may be inserted through the retaining member. An additional feature of the method of repairing severed nerves is that the expanded tail may be formed by heating the second end of the suture and shaping the second end into the expanded tail.

In accordance with the invention the foregoing advantages have also been achieved through the present method of adjoining severed nerve ends comprising the steps of: providing a first severed nerve end and a second severed nerve end; aligning first severed nerve end and second severed nerve end; inserting through first severed nerve end and second severed nerve end a suture, wherein the suture includes an expanded tail; securing the expanded tail of the suture to either the first severed nerve end or the second severed nerve end; placing a retaining member and the suture within a clip; and capturing the retaining member and the suture within the clip thereby adjoining first severed nerve end and second severed nerve end.

A further feature of the method of adjoining severed nerve ends is that the first or second severed nerve end may be located on a nerve graft.

The surgical systems for repairing severed nerves, methods of repairing severed nerves, and methods of adjoining severed nerves of the present invention have the advantages of: increasing the visibility of the anastomotic site thereby facilitating proper alignment of the severed nerve ends; and decreasing trauma to the severed nerve ends thereby facilitating healing of the severed nerve. As mentioned above, it is believed that the present invention will achieve these objectives and overcome the disadvantages of other surgical systems and methods in the field of the invention, but its results or effects are still dependent upon the skill and training of the operators and surgeons.

Figure 1:
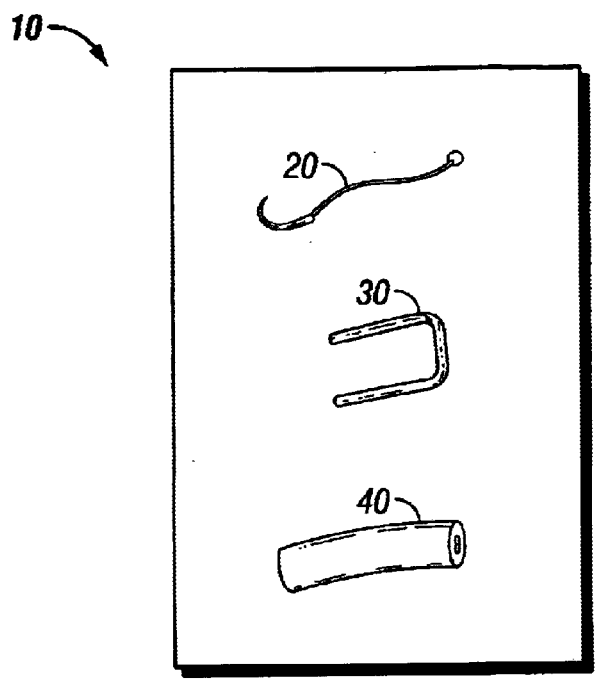
FIG. 1 is a perspective view of one specific embodiment of the surgical system for repairing severed nerves of the present invention.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION AND SPECIFIC EMBODIMENTS

The present invention is directed to a surgical system, or kit, for repairing severed ends of a damaged nerve. The surgical system may be used to adjoin the ends of a severed nerve or adjoin the ends of a severed nerve and the ends of a nerve graft. A nerve graft may be a nerve from a donor, or another nerve located within the body containing the severed nerve. The surgical system may also be used to repair severed nerves.

Referring now to FIGS. 1–4, in one embodiment of the present invention, a surgical system includes a suture 20, a surgical vessel clip, or clip, 30 and a guide, or retaining member 40. Suture 20 has a first end 21 and a second end 22. First end 21 is connected to a needle 23. Second end 22 preferably includes an expanded tail 24.

Suture 20 includes a length 25 that may be any measurement desired or necessary to suture the nerve. In one specific embodiment, suture 20 is approximately 1.5 inches, or long. Further, suture 20 may be made out of any material known to persons skilled in the art. Preferably, suture 20 is a microsuture manufactured out of nylon or prolene and needle 23 is stainless steel. A preferred suture readily available to surgeons is the 7-0 monofilament nylon suture.

Figure 2:
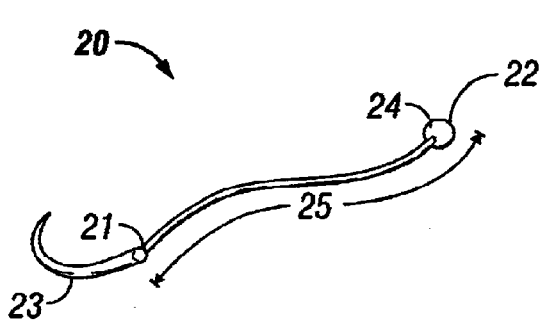
FIG. 2 is a side view of a suture of the surgical system shown in FIG. 1.
Figure 3:
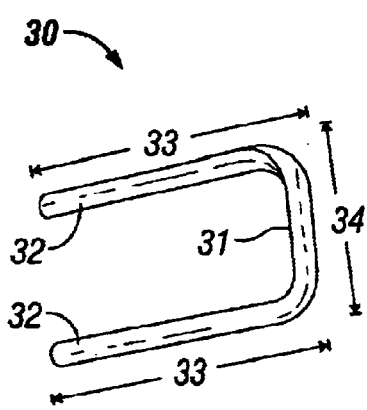
FIG. 3 is a perspective view of the clip of the surgical system shown in FIG. 1.
Figure 4:
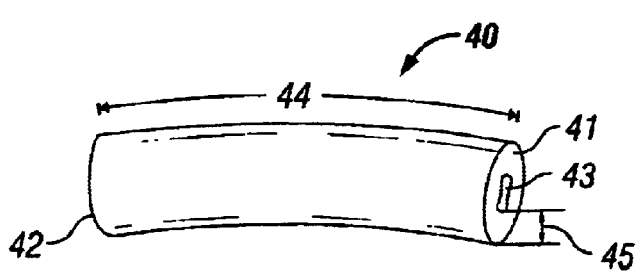
FIG. 4 is a perspective view of the retaining member of the surgical system shown in FIG. 1.

Clip 30 includes support member 31 having length 34 and at least one arm 32 having length 33. As shown in FIGS. 1 and 2, clip 30 includes two arms 32. Support member 31 and arm 32 may be any size or shape desired or necessary to facilitate repairing severed nerves and adjoining severed nerve ends as discussed in more detail below. In a preferred embodiment, clip 30 includes support member 31 having length 34 of about 7.5 millimeters and two arms 32 having equal lengths 33 of about 2.5 millimeters.

Clip 30 may be formed out of any material known to persons skilled in the art. Suitable materials for forming clip 30 include plastic, metal, and absorbable materials, such as polymers or copolymers which are discussed in greater detail below with respect to retaining member 40.

Retaining member 40 includes a first end 41, a second end 42, and a length 44. Retaining member 40 may be any shape and size desired or necessary to adjoin severed nerve ends and to facilitate capturing suture 20. For example, length 44 may be in the range from about 2 millimeters to about 6 millimeters. Generally, length 44 is about 3 millimeters.

As shown in FIGS. 1–4, retaining member 40 is cylindrically shaped having cavity 43 disposed between first end 41 and second end 42 of retaining member 40. Cavity 43 defines thickness 45. In this embodiment, cavity 43 has a diameter 46 in the range from about 0.5 millimeters to 2.0 millimeters, and thickness 45 in the range from about 0.1 millimeters to 0.5 millimeters.

Additionally, retaining member 40 may be formed out of any material known to persons of ordinary skill in the art. For example, retaining member 40 may be formed from plastic, silicone, metal, or polymers or copolymers. Preferably, retaining member 40 is formed out of absorbable polymer or copolymer. Suitable polymers and copolymers for use in forming retaining member 40 are any polymer or copolymer in woven or nonwoven fibrous form stiffened with a binder polymer or bonded together by heating, or particulate form which may be sintered or otherwise bonded together, to give a porous structure. Preferably, the texture of the retaining member 40 is not smooth, thereby facilitating the ability of the retaining member 40 to prevent suture 20 from slipping out of clip 30. While absorbable or nonabsorbable polymers can be used, preferably, absorbable polymers or copolymers, or mixtures of absorbable polymers or copolymers, form retaining member 40.

Preferred polymers and copolymers are polylactic acid, polyglycolic acid, polydioxanone, poly(lactide-co-glycolide) and poly(esteramides) such as poly(oxysuccinoyloxydodecane-1,12-di(amidocarbonylmethylene)-co-10-percent-oxysuccinoyloxy-4,9-dioxadodecane-1,12-di(amidocarbonylmethylene) and poly[oxysuccinoyloxyhexane1,6-di(amidocarbonylmethylene)], and mixtures thereof.

Body-absorbable, thermoplastic, binder polymers used to stiffen woven or nonwoven fibrous polymeric materials in retaining member 40 include polylactic acid and polyesteramides such as poly(oxysuccinoyloxydodecane-1,12-di(amidocarbonylmethylene)-co-10 percent-oxysuccinoyloxy-4,9-dioxadodecane-1,12-di(amidocarbonylmethylene), poly[oxysuccinoyloxyhexane-1,6-di(amidocarbonylmethylene)] and other polyesteramides.

In a preferred embodiment, retaining member 40 is cylindrically, or tube, shaped thereby forming a sheath, and is formed of polyglycolic acid.

Figure 5:
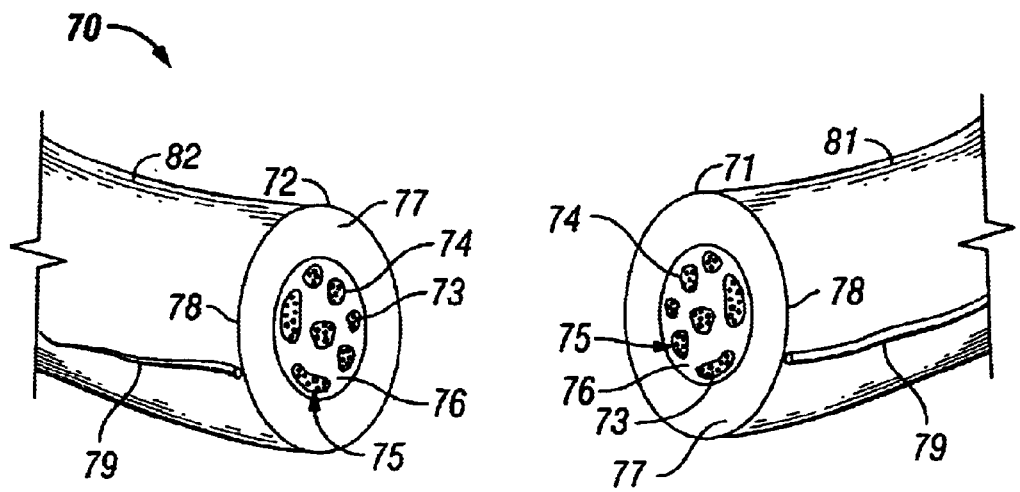
FIG. 5 is a perspective cross-sectional view of a severed nerve.
Figure 6:
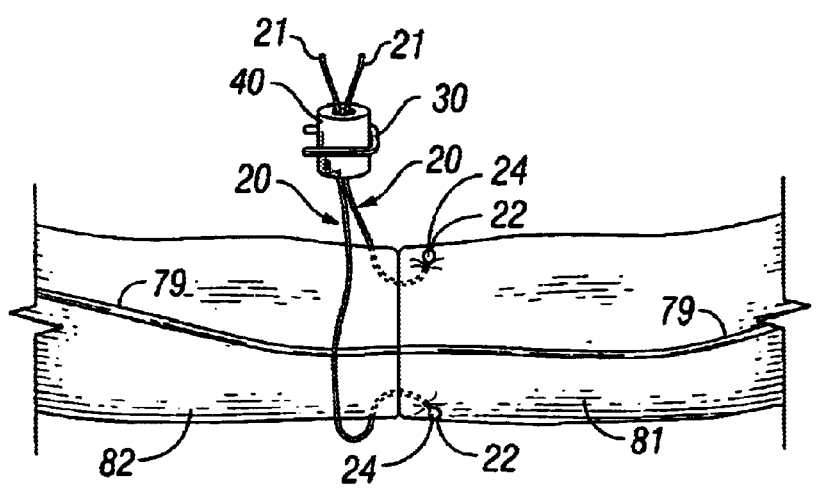
FIG. 6 is a perspective view of two nerve ends adjoined by the surgical system shown in FIG. 1.

Referring now to FIGS. 5 and 6, severed nerve 70 includes a first severed end 71 located on a first nerve trunk 81 and a second severed end 72 located on a second nerve trunk 82. It is to be understood that either first nerve trunk 81 or second nerve trunk 82 may be a nerve graft. Nerve 70 is formed by nerve fibers 73 and endoneurium 74. Endoneurium 74 is connective tissue fibers that holds the nerve fibers 73 together. The nerve fibers 73 and endoneurium 74 form a fasciculus 75. The fasciculus 75 is surrounded by a sheath of connective tissue called perineurium 76. The perineurium 76, and thus the fasciculus 75, is enclosed in a thick sheath of connective tissue called the epineurium 77 that may also include fat cells (not shown). In some instances, blood vessels 79 are disposed along the length of epineurium 77.

In one specific embodiment of the present invention shown in FIGS. 5 and 6, a severed nerve 70 is reattached, i.e., the first end 71 and the second end 72 of severed nerve 70 are aligned and then adjoined. Alignment of first end 71 and second end 72 may be accomplished by visually inspecting the fasciculi 75 at each of first end 71 and second end 72 and aligning each fasciculus 75 at first end 71 with an alike shaped fasciculus 75 at second end 72. Alternatively, alignment of first end 71 and second end 72 may be accomplished by aligning blood vessels 79.

A suture 20, having a needle 23 disposed at first end 21, is prepared by forming an expanded tail 24 on the second end 22 of suture 20. In one embodiment, expanded tail 24 is prepared by deforming second end 22 of suture 20 such as by applying heat to second end 22, i.e., melting second end 22, and shaping second end 22 into expanded tail 24. Preferably, expanded tail 24 is formed prior to the patient being brought into the operating room. Further, length 25 of suture 20 is preferably not altered significantly during the formation of expanded tail 24 such that length 25 of suture 20 is approximately 1.5 inches.

Needle 23 of suture 20 is inserted through the epineurium 77 of first end 71 and second end 72 of nerve 70. Suture 20 is then pulled through epineurium 77 of first end 71 and second end 72 until expanded tail 24 is flush with epineurial edge 78 of epineurium 77 of either first end 71 or second end 72, thereby adjoining first end 71 and second end. Suture 20 may be inserted through epineurium 77 of first end 71 and second end 72 as many times as desired of necessary to sufficiently maintained first end 71 adjoined to second end 72 in the desired alignment to optimize the chances of full recovery of functionality of nerve 70. Alternatively, as shown in FIG. 6, a second suture 20 may be inserted through epineurium 77 of first end 71 and second end 72 of severed nerve 70 to assist in maintaining first end 71 adjoined to second end 72 in the desired alignment.

After suture 20 is inserted through epineurium 77 of first end 71 and second end 72 of severed nerve 70, needle 23 is removed from first end 21 suture 20 by cutting suture 20 with scissors or other sharp tool. First end 21 is then placed next to retaining member 40. Preferably, as shown in FIG. 6, retaining member 40 is cylindrically, or tubed, shaped and first end 21 is placed through retaining member 40.

Clip 30 is placed around retaining member 40, and thus suture 20, thereby securing suture and retaining member 40 within clip 30. In this arrangement, first end 71 and second end 72 are adjoined in an anatomic coaptation and immobilization of first end 71 adjoined to second end 72 in the alignment desired by the surgeon. Preferably, clip 30 is formed of malleable material such that after suture 20 and retaining member 40 are within clip 30, clip 30 may be deformed to secure, or clamp, suture 20 and retaining member 40 within clip 30.

In the embodiment in which a nerve graft is secured to two ends of a severed nerve, the method described above is repeated for both ends of the nerve graft.

It is to be understood that the invention is not limited to the exact details of construction, operation, exact materials, or embodiments shown and described, as obvious modifications and equivalents will be apparent to one skilled in the art. For example, the surgical system and method for adjoining severed nerve ends, and method for repairing severed ends of a damaged nerve may include grafting a donor nerve with the severed nerve. In other words, a first end of a nerve graft may be connected to a first end of a severed nerve and a second end of the nerve graft may be connected to a second end of the severed nerve. Accordingly, the invention is therefore to be limited only by the scope of the appended claims.

What is claimed:

1. A surgical system for repairing severed nerves comprising:
   at least one suture having a first end and a second end;
   at least one clip having a support member and at least one arm having a length; and
   at least one retaining member having a first end and a second end.

2. The surgical system for repairing severed nerves of claim 1, wherein the first end of the suture includes a needle.

3. The surgical system for repairing severed nerves of claim 1, wherein the second end of the suture includes an expanded tail.

4. The surgical system for repairing severed nerves of claim 1, wherein the clip is formed out of metal.

5. The surgical system for repairing severed nerves of claim 1, wherein the clip is formed out of plastic.

6. The surgical system for repairing severed nerves of claim 1, wherein the clip is formed out of an absorbable polymer or copolymer.

7. The surgical system for repairing severed nerves of claim 1, wherein the retaining member is formed out of plastic.

8. The surgical system for repairing severed nerves of claim 1, wherein the retaining member is formed out of an absorbable polymer or copolymer.

9. The surgical system for repairing severed nerves of claim 1, the clip includes two arms.

10. The surgical system for repairing severed nerves of claim 9, wherein each of the two arms include a length of about 2.5 millimeters.

11. The surgical system for repairing severed nerves of claim 10, wherein the support member includes a length of about 1.5 millimeters.

12. The surgical system for repairing severed nerve ends of claim 1, wherein the retaining member includes a length of about 3.0 millimeters.

13. The surgical system for repairing severed nerves of claim 1, wherein the suture includes a length of about 3.0 centimeters.

14. A method of repairing severed nerves comprising the steps of:
   providing a severed nerve having a first severed end and a second severed end;
   forming a suture having a first end and a second end, wherein the first end includes a needle and the second end includes an expanded tail;
   aligning the first severed end with the second severed end;
   inserting the needle through the first and second severed ends;
   securing the expanded tail of the suture to either the first severed end or the second severed end;
   removing the needle from the first end of the suture;
   placing the first end of the suture and a retaining member within a clip; and
   capturing the first end of the suture and the retaining member within the clip.

15. The method of repairing severed nerves of claim 14, wherein the first end of the suture and the retaining member are captured within the clip by deforming the clip.

16. The method of repairing severed nerves of claim 14, wherein the first end of the suture is inserted through the retaining member.

17. The method of repairing severed nerves of claim 14, wherein the expanded tail is formed by heating the second end of the suture and shaping the second end into the expanded tail.

18. A method of adjoining at severed nerve ends comprising the steps of:
   providing a first severed nerve end and a second severed nerve end;
   aligning first severed nerve end and second severed nerve end;
   inserting through first severed nerve end and second severed nerve end a suture, wherein the suture includes an expanded tail;
   securing the expanded tail of the suture to either the first severed nerve end or the second severed nerve end;
   placing a retaining member and the suture within a clip; and
   capturing the retaining member and the suture within the clip thereby adjoining first severed nerve end and second severed nerve end.

19. The method of claim 18, wherein first or second severed nerve end is located on a nerve graft.

* * * * *